United States Patent [19]
Ruiz

[11] Patent Number: 5,213,812
[45] Date of Patent: May 25, 1993

[54] PREPARATION PROCESS OF SUSTAINED RELEASE COMPOSITIONS AND THE COMPOSITIONS THUS OBTAINED

[75] Inventor: Jean-Marc Ruiz, Trelaze, France

[73] Assignee: Societe de Conseils de Recherches et d'Applications Scientifiques (S.C.R.A.S.), France

[21] Appl. No.: 734,493

[22] Filed: Jul. 23, 1991

[30] Foreign Application Priority Data

Aug. 1, 1990 [GB] United Kingdom ............... 9016885

[51] Int. Cl.$^5$ ............................................. A61K 9/16
[52] U.S. Cl. .................................. 424/499; 424/501
[58] Field of Search ............ 424/461, 497, 499, 464, 424/501

[56] References Cited

U.S. PATENT DOCUMENTS

| | | |
|---|---|---|
| 4,010,125 | 3/1977 | Schally et al. ............... 260/8 |
| 4,675,189 | 6/1987 | Kent et al. ............... 424/490 |
| 4,767,628 | 8/1988 | Hutchinson ............... 424/426 |
| 4,844,910 | 4/1989 | Leslie ............... 424/497 |
| 4,867,985 | 9/1989 | Heafield ............... 424/461 |

FOREIGN PATENT DOCUMENTS 0058481 10/1986 European Pat. Off. .

*Primary Examiner*—Thurman K. Page
*Assistant Examiner*—William E. Benston, Jr.
*Attorney, Agent, or Firm*—Lucas & Just

[57] ABSTRACT

The invention relates to a preparation process of particles designed to release an effective amount of active ingredient over a predetermined period of time, said particles comprising one ore more active ingredients in admixture with a bioresorbable and/or biodegradable polymer or copolymer, and the particles thus obtained in a substantially spheroidal form and substantially deprived of active ingredient on the external covering.

35 Claims, No Drawings

PREPARATION PROCESS OF SUSTAINED RELEASE COMPOSITIONS AND THE COMPOSITIONS THUS OBTAINED

The invention relates to a preparation process of particles designed to release an effective amount of active ingredient over a predetermined period of time, said particles comprising one or more active ingredients in admixture with a bioresorbable and/or biodegradable polymer or copolymer. In this specification, the term "active ingredient" is used to mean any therapeutically active substance or admixture which might advantageously be administered to man or other animals for the purpose of diagnosis, cure, mitigation, treatment or the prevention of disease.

Preparation processes of microparticles as sustained release compositions, are well known. In the state of the art, microcapsules and microspheres are described as pharmaceutical compositions for the substained release of one or more active ingredients.

The microcapsules are generally obtained by suspending or dissolving a polymer and/or copolymer in a solution and then evacuating the solvent; microcapsules are formed by a core with a rather high active ingredient content surrounded by a covering with a rather high polymer and/or copolymer content. Because complete solvent elimination is never possible, microcapsules contain at least traces of solvents in their composition; although, by this way, the encapsulation rate with respect to the active ingredient never reaches 100%.

The microspheres are microparticles also generally formed using solvents and present a more regular repartition of the active ingredient in the polymer; the second step of their formation, e.g. extrusion and grinding, implies the formation of an irregular external surface in any non-spheroidal form. The presence of active ingredient on the external surface and the irregularity of the said surface do not permit precise control of the burst effect. Moreover as solvent has been used in the first step, the complete elimination is practically impossible.

In contradistinction, the particles according to the present invention, which may be called microballs, are processed in a dry way without use of any solvent. The solid composition obtained by admixing the active ingredient and the polymer in the dry way, is manufactured by conventional techniques well known in the pharmaceutical art. The repartition of the active ingredient in the polymer is approximately the same as the above defined microspheres. After grinding and sifting, the particles are suspended in a gel under energetic stirring; then the mixture is heated with close control of temperature and time according to the employed constituents. The suspended particles fuse, and due to superficial tension tend to become spherical if the gel viscosity is sufficient; the viscosity must be such as to avoid agglomeration. This operation may be called by the name of "spheronization". When spheronization has been achieved, the suspension is very rapidly cooled (by dipping), and the gel is dissociated by addition of a washing agent which is neither a solvent of the polymer nor a solvent of the active ingredient. The smooth structure of the surface of the microballs ensures no retention of the washing agent.

The microballs of the invention are bioresorbable, non irritating pharmaceutical compositions consisting of one or more active ingredients intimately dispersed in a bioresorbable polymer designed to release an effective amount of active ingredient over a predetermined period of time.

The microballs permit prolonged release of active ingredients for a controlled period of time from the sites of parenteral administration and minimize the frequency and thus the discomfort and inconvenience associated with conventional daily injection formulations. Unlike conventional depot injections, the microballs according to the invention undergo biodegradation in the body into normal or essentially normal metabolic products, are non reactive toward body tissues, and can be designed by controlling the average molecular weight in weight and the average molecular weight in number, to undergo hydrolysis and to release the active ingredient from the depot at a desired rate.

The invention relates to a preparation process of particles designed to release an effective amount of active ingredient over a predetermined period of time, said particles comprising one or more active ingredients in admixture with a bioresorbable and/or biodegradable polymer or copolymer and appropriate pharmaceutical additives, and the size of said particles being comprised between specific limits, said particle manufacturing process including, in the first phase, a processing of the particles by usual routes well known in the art comprising a step for the mixture of the components, a step for tabletting and/or extruding the resulting mixture, a step of grinding the same, and a step of selecting the appropriate size range for the particles, wherein, in the first phase, the components are mixed in the dry state and that the first phase is followed by a second phase consisting in treating particles obtained in the first phase by suspending the same under stirring in a gel which is a solvent for none of the components, and having a viscosity, at 60° C. or over, (the upper temperature limit being defined by the stability of components), either of from about 40 to about 500 mPa.s, wherein hydrophilic gel is used, or of from about 3,000 to about 12,500 mPa.s wherein hydrophobic gel is used; heating the gel to a temperature sufficient to melt the particles whereby microballs are formed; cooling the gel; and recovering the microballs by filtration.

The gel viscosity may be preferably comprised at 60° C. or over, of from about 80 to about 200 mPa.s wherein hydrophilic gel is used, and of from 5,000 to 11,000 mPa.s wherein hydrophobic gel is used, and in a preferred embodiment, at about 100 mPa.s wherein hydrophilic gel is used and about 9,000 mPa.s wherein hydrophobic gel is used.

The invention relates also to microballs thus obtained, in a substantially spheroidal form and deprived of active ingredient on the external covering.

Pharmaceutically inert additives which can be ground with the polymer or copolymer include PvP, mannitol, carbowax, polyethylene glycols, glycerides and ethyl cellulose.

The melting, as previously stated, is at a temperature in excess of the glass temperature. For example, for a D,L lactic acid-co-glycolic acid copolymer (50:50), temperature may be about 75° C. The process provides classical tablets or others forms well known in the pharmaceutical art, which may be cut to lengths of, e.g., 1 cm for grinding. Grinding may be effected with a congealed grinding apparatus.

The gel may be hydrophobic or hydrophilic. Hydrophilic gels, such as PvP, carboxymethyl cellulose, poloxamer and water, are suitable for hydrophobic active ingredients and are common for industrial use.

Stirring must be maintained throughout the suspension of the active ingredient polymer mixture in the gel, essentially at the beginning of the process to disperse particles in the gel. Filtration may be through a 0.45 to 10 μm PTFE membrane for instance when preparation for injection is involved.

In the process of the invention only mechanical systems are used. The process of the invention is different from spray atomisation, pan coating, fluid bed coating, microencapsulation by coacervation and microencapsulation by solvent evaporation, none of which processes leads to homogeneous microballs.

Classes of active ingredient which may be used in the invention include agents affecting the central nervous system, e.g. narcotics such as morphine; narcotic antagonists, such as naloxone; antipsychotic agents, such as sodium pentobarbital, chlorpromazine; antidepressives such as imipramine hydrochloride; stimulants, such as methyl phenadate and nikethamide; hallucinogens, analgesics such as mumorphan meperidine and anorexigenic agents.

Other classes are pharmacodynamic agents, e.g. antihypertensive agents such as reserpine, and antianginal agents, such as papaverine, and drugs for the therapy of pulmonary disorders, such as theophylline ethylene diamine salt. Additional classes are chemotherapeutic agents, e.g. antiviral; antiparasitic, such as emetine hydrochloride; antifungal agents, such as cyclohexemide; and anti-neoplastic agents, such as triethylene thiophosphoramide; agents affecting metabolic diseases and endocrine functions, e.g., prostaglandins; athersclerosins,- such as heparin; steroids and biologically related compounds; polypeptides, such as bacitracin, polymyxin B sulfate; natural and synthetic hormones, such as progesterone; steroid and non steroidal anti-inflammatory agents, such as hydrocortisone; and agents affecting thrombosis, such as crystalline trypsin; vitamins, such as vitamin B12; anti-epilepsy agents, such as phenobarbital, and the like. It should be understood that the specific drugs mentioned by name are illustrative and not limitative.

Endocrine agents comprise a particularly useful class of compounds in this invention and can be defined either as natural hormones or as synthetic drugs that to some extent act like, or antagonize, natural hormones, such as triptoreline or somatuline. Endocrine agents include, but are not limited to, both steroids and non steroids that function as fertility control agents; progestogens, estrogens, androgens, antiandrogens, corticoids, anabolic agents and anti-inflammatory agents.

Any biodegradable polymer can be used for the microball formulation. Illustrative, but non-limiting, examples include:
homopolymers and copolymers of ε-caprolactone
denatured proteins
homopolymers and copolymers of lactic acid and glycolic acid
poly ortho esters
poly anhydrides
poly (β-hydroxybutyric acid)
poly phosphazens
poly alkylcyanoacrylates
polycetals
poly saccharides, cellulosic polymers
polypeptides When glycolic or lactic acids are used to prepare the polymer, it is clear that the polymer's hydrolysis products will include glycolic or lactic acids which are normal metabolites of the body. When the polymer is prepared from the other compounds listed above, the hydrolysis products will be related in simple structure and will have no deleterious or untoward effect on the body.

Polymers and copolymers useful in the formulations of the invention may be prepared by the methods disclosed in U.S. Pat. Nos. 2703316, 2758987 and EP 0244114.

For this invention, different polymer parameters have been known for a good processing:
the crystallinity,
the amount and type of catalyst,
the degree of polymerization,
the average molecular weight in weight and in number,
the polydispersity value, which corresponds to the ratio between the average molecular weight in weight and number,
the glass temperature, or Tg.

This ultimate parameter is important for the melting in a gelified vehicle. A control of the microball release profile is possible with polymer parameters listed above.

The relative proportions of the active ingredient and polymer can be varied over a wide range depending on the desired effect. The active ingredient can be present in an amount which will be released over controlled periods of time. This necessarily implies a quantity of active ingredient greater than the conventional single dose.

Proportions may range from 1 percent of active ingredient and 99 percent of the polymer to 99 percent of active ingredient and 1 percent of polymer. Ratios which have shown good results include 1 part of active ingredient to from 10 to 30 parts of polymer.

Pharmacokinetic results obtained by use of microballs, according to the invention, are unusually good, compared either to non spheroidal particles, or microcapsules prepared by usual methods. Microcapsules when parenterally administered to rats, present a release profile which is essentially biphasic with a "plateau" phase over a period of 20 days for triptoreline; the first phase presents an important active ingredient release, due to physiological fluid washing. The second phase is a sustained release of an effective amount of the active ingredient with a "plateau" phase. The duration of the "plateau" phase depends on the associated active ingredient-polymer.

The microballs, according to the invention, present a limited burst effect compared to non spheroidal particles and allow in an aqueous physiological environment, an advantageous sustained release of active ingredient.

A Scanning Electron Microscopy study shows that the microball surface is homogeneous without non-microencapsulated active ingredient crystals.

The composition of the invention may be formulated for injection by syringe into subcutaneous cellular tissue or muscular tissue, by suspending the microballs in a liquid vehicle. Suitable liquid vehicles include water, normal sodium chloride solution and oils such as sesame oil, peanut oil and vegetable oil. Adjuvants may be added as necessary or desirable. These may include dispersing agents such as polysorbate 80, thickening agents such as carboxymethyl cellulose, preservatives such as chlorbutanol or methyl paraben or propyl paraben, and suspending agents such as aluminium monostearate. Other adjuvants such as benzyl alcohol can also be included.

The invention will be better understood from the description of the following examples.

EXAMPLE 1

In this example and also in examples 2 to 4 and 7 to 13, a poly (lactide-co-glycolide) was used with the following characteristics:

polymer inherent viscosity range in chloroform (0.1% w/v) : 0.1–5.0 dl/g
proportion of lactide (D,L or L) : 50 to 100 %
proportion of glycolide: 0 to 50 %
average molecular weight range
$\overline{Mw}$: 1000 to 200 000
$\overline{Mn}$: 100 to 100 000
polydispersity value range P: 2 to 10

Poly (D,L lactide-co-glycolide) 50/50 [η inh 0.4 dl/g in chloroform (0.1 % w/v); Tg : 40° C. by DSC (differential scanning calorimetry)]. 10 g was ground and mixed with 250 mg of D-Trp6 LHRH Acetate. The mixture was melted at 75° C. Tablets were ground. Resulting particles 0.5 to 200 microns in size were suspended in a carboxymethyl cellulose Na gel (10% w/w in pure water).

Controlled heating (20° C., 80° C., 20° C.) allows a progressive melting of the particles which become microcapsules of PLGA 50/50 containing a hormone analog.

EXAMPLE 2

Poly (D,L lactide-co-glycolide) 50/50 [η inh: 0.8 dl/g in chloroform; Tg: 44° C. by DSC] 10 g was similarly used with 1 g of D-Trp6 LHRH Acetate.

EXAMPLE 3

Poly (D, L lactide-co-glycolide) 50/50 [η inh: 0.4 dl/g in chloroform; Tg: 40° C. by DSC] 10 g was similarly used with 250 mg of D-Trp6 LHRH Pamoate.

EXAMPLE 4

Poly (D,L lactide-co-glycolide) 50/50 [η inh : 0.8 dl/g in chloroform; Tg: 44° C. by DSC] 10 g was similarly used with 1 g of D-Trp6 LHRH Pamoate.

EXAMPLE 5

Poly-L-Lactide [η inh:1.2 dl/g in chloroform; Tg=60° C. by DSC] 10 g was similarly used with 1.8 g of Somatuline Acetate. Melting temperature is a little higher:85° C.

EXAMPLE 6

Poly-L-Lactide [η inh:1.2 dl/g in chloroform; Tg:60° C. by DSC] 10 g was similarly used with 1.8 g of Somatuline Pamoate.

EXAMPLE 7

Poly (D,L lactide-co-glycolide) 75/25 [η inh: 1.03 dl/g in chloroform Tg: 55° C. by DSC] 10 g was similarly used with 1 g of D-Trp6 LHRH Acetate. Melting temperature is 82° C.

EXAMPLE 8

Poly (D,L lactide-co-glycolide) 50/50 [η inh:0.8 dl/g in chloroform; Tg:44° C. by DSC] 10 g was similarly used with 1.4 g of corticotropine (ACTH 1-39).

EXAMPLE 9

Poly (D,L lactide-co-glycolide) 50/50 [η inh:0.8 dl/g in chloroform; Tg:44° C. by DSC] 10 g was similarly used with 250 mg of D-Trp6 LHRH Acetate spray dried.

EXAMPLE 10

Poly (D,L lactide-co-glycolide) 50/50 [η inh:0.8 dl/g in chloroform; Tg:44° C. by DSC] 10 g was similarly used with 1.8 g of Somatuline Acetate spray dried.

EXAMPLE 11

Poly (D,L lactide-co-glycolide) 50/50 [η inh:0.8 dl/g in chloroform; Tg:44° C. by DSC] 10 g was similarly used with 500 mg of [D-Trp6, des GlylO] - LHRH Ethylamide.

EXAMPLE 12

Poly (D,L lactide-co-glycolide) 50/50 [η inh:0.8 dl/g in chloroform; Tg:44° C. by DSC] 10 g was similarly used with 250 mg of Nafareline Acetate.

EXAMPLE 13

Poly (D,L lactide-co-glycolide) 50/50 [η inh:0.4 dl/g in chloroform (0.1 % w/v); Tg:40° C. by DSC] 10 g was ground and mixed with 250 mg of D-Trp6 LHRH Acetate. The mixture was melted at 75° C. Tablets were ground. Resulting particles 0.5 to 200 microns in size are suspended in silicone oil (viscosity:corresponding to 9 000 mPa.s at 60° C.). Controlled heating (20° C., 80° C., 20° C.) allows a progressive melting of the particles which become microballs of PLGA 50/50 containing an hormone analog.

EXAMPLE 14

Poly (ε-caprolactone-co-D, L lactide) 20/80 [η inh: 0.5 dl/g in chloroform; Tg:18° C. by DSC] 10 g was similarly used with 250 mg of D-Trp6 LHRH Acetate. Melting temperature is lower:35° C.

I claim:

1. A method of preparing microballs which release an active ingredient over a period of time, said method comprising:
   (a) forming a dry mixture comprising at least one active ingredient with a polymer material selected from the group consisting of bioresorbable polymers, bioresorbable copolymers, biodegradable polymers, biodegradable copolymers, and combinations of the foregoing, the amount of active ingredient in the mixture material being from 1 percent to 99 percent and the amount of polymer material being from 99 percent to 1 percent;
   (b) subjecting said mixture to a step selected from the group consisting of tabletting, extruding and a combination of tabletting and extruding;
   (c) grinding the product of step (b) to form mixture microparticles;
   (d) suspending the said mixture microparticles in a gel by stirring, said gel being selected from the group consisting of: a hydrophilic gel having a viscosity at a temperature between at least 60° C. and a temperature below the temperature at which the components of the mixture are no longer stable of about 40 to about 500 mPa.s; and, a hydrophobic gel having a viscosity at a temperature between at least 60° C. and a temperature below the temperature at which which the components of the mixture are no longer stable of about 3,000 to about 12,500 mPa.s;

(e) heating a gel to a temperature above the Tg of the said polymer material and sufficient to melt the mixture particles in the gel and form microballs;

(f) cooling the gel to a temperature at which the microballs can be separated from the gel; and (g) separating the microballs from the gel by filtration.

2. The method of claim 1 wherein the said mixture of step (a) further includes at least one additive selected from the group consisting of PvP, mannitol, polyethylene glycols, glycerides, and ethyl cellulose.

3. The method of claim 1 wherein the polymer material is lactic acid-co-glycolic acid copolymer.

4. The method of claim 1 wherein the active ingredient is an LHRH analog.

5. The method of claim 1 wherein the active ingredient is selected from the group consisting of: D-Trp6 LHRH acetate; D-Trp6 LHRH pamoater; somatuline acetate; somatuline pamoate; corticotropine; [D-Trp 6, des Gly10]-LHRH ethylaminde; and nafareline acetate.

6. The method of claim 3 wherein the active ingredient is D-Trp6 LHRH pamoate.

7. A method of preparing microballs which release an active ingredient over a period of time, said method comprising:

(a) forming a dry mixture comprising at least one LHRH analog with a polymer material which is a poly-(D,L-lactide-co-glycolide) having a Tg of 40° C. by DSC, the amount of LHRH analog in the mixture material being from 1 percent to 99 percent and the amount of polymer material being from 99 percent to 1 percent;

(b) subjecting said mixture to a step selected from the group consisting of tabletting, extruding and a combination of tabletting and extruding;

(c) grinding the product of step (b) to form mixture microparticles of 0.5 to 200 microns;

(d) suspending the said mixture microparticles in a gel by stirring, said gel being selected from the group consisting of a hydrophilic gel having a viscosity at a temperature between at least 60° C. and a temperature below the temperature at which the components of the mixture are no longer stable of about 40 to about 500 mPa.s; and, a hydrophobic gel having a viscosity at a temperature between at least 60° C. and a temperature below the temperature at which the components of the mixture are no longer stable of about 3,000 to about 12,500 mPa.s;

(e) heating the gel to a temperature above the Tg of the said polymer material and sufficient to melt the mixture particles in the gel and form microballs;

(f) cooling the gel to a temperature at which the microballs can be separated from the gel; and (g) separating the microballs from the gel by filtration.

8. The method of claim 7 wherein the heating of step (e) is to a temperature of at least 80° C. and the cooling of step (f) is to a temperature not above 20° C.

9. The method of claim 7 wherein the LHRH analog is D-Trp6 LHRH pamoate.

10. The method of claim 7 wherein the polymer material is 50-99 percent lactide and 1-50 percent glycolide.

11. The method of claim 7 wherein the polymer material if 50% lactide and 50% glycolide.

12. The method of claim 8 wherein the said mixture of step (a) further includes at least one additive selected from the group consisting of PVP, mannitol, polyethylene glycols, glycerides, and ethyl cellulose.

13. The method of claim 1 wherein a hydrophilic gel is used and the gel viscosity is from about 80 to about 200 mPa.s.

14. The method of claim 13, wherein the gel viscosity is about 100 mPa.s.

15. The method of claim 1 wherein a hydrophobic gel is used and the gel viscosity is from about 5,000 to about 11,000 mPa.s.

16. The method of claim 13 wherein the gel viscosity is about 9,000 mPa.s.

17. Microballs prepared according to claim 1 in a spheroidal form and the amount of active ingredient at the surface being sufficient to allow a release profile which is essentially biphasic.

18. Microballs prepared according to claim 13 in a spheroidal form and the amount of active ingredient at the surface being sufficient to allow a release profile which is essentially biphasic.

19. Microballs prepared according to claim 15 in a spheroidal form and the amount of active ingredient at the surface being sufficient to allow a release profile which is essentially biphasic.

20. Microballs prepared according to claim 14 in a spheroidal form and the amount of active ingredient at the surface being sufficient to allow a release profile which is essentially biphasic.

21. Microballs prepared according to claim 16 in a spheroidal form and the amount of active ingredient at the surface being sufficient to allow a release profile which is essentially biphasic.

22. Microballs prepared according to claim 7 in a spheroidal form and the amount of active ingredient at the surface being sufficient to allow a release profile which is essentially biphasic.

23. In microparticles comprising 1-99 percent polymer material and 99-1 percent active ingredient, the improvement comprising said microparticles being spheroidal and the amount of active ingredient at the surface being sufficient to allow a release profile which is essentially biphasic.

24. The microparticles of claim 23 wherein the copolymer material is selected from the group consisting of bioresorbable polymers, bioresorbable copolymers, biodegradable polymers, biodegradable copolymers, and combinations of the foregoing.

25. The microparticles of claim 23 further including at least one additive selected from the group consisting of PvP, mannitol, polyethylene glycols, glycerides, and ethyl cellulose.

26. The microparticles of claim 23 wherein the polymer material is lactic acid-co-glycolic acid copolymer.

27. The microparticles of claim 26 wherein the active ingredient is D-Trp6 LHRH pamoate.

28. The microparticles of claim 23 wherein the active ingredient is an LHRH analog.

29. The microparticles of claim 23 wherein the active ingredient is selected from the group consisting of: D-Trp6 LHRH acetate; D-Trp6 LHRH pamoate; somatuline acetate; somatuline pamoate; corticotropine; [D-Trp6, des Gly10]-LHRH ethylamide; and nafareline acetate.

30. The microparticles of claim 23 wherein the microparticles comprise 10-30 parts polymer material to 1 part active ingredient.

31. In microparticles comprising 1-99 percent polymer material and 99-1 percent active ingredient, the improvement comprising said microparticles being spheroidal and the external surface of the spheroidal microparticles being substantially free of active ingredient and wherein the polymer material is 50-99 percent lactide and 1-50 percent glycolide.

32. In microparticles comprising 1-99 percent polymer material and 99-1 percent active ingredient, the improvement comprising said microparticles being spheroidal and the external surface of the spheroidal microparticles being substantially free of active ingredient and wherein the polymer material is 50% lactide and 50% glycolide.

33. Microballs comprising a polymer material and an active ingredient, said polymer material being a lactic acid-co-glycolic acid copolymer, said copolymer being 50-99 percent lactide and 1-50 percent glycolide, said active ingredient being D-Trp6 LHRH pamoate, the ratio of said active ingredient to said polymer material being from 1:10 to 1:30, said microballs being in spheroidal form and the external surface of the spheroidal microballs being substantially free of said active ingredient.

34. The microballs of claim 33 further including at least one additive selected from the group consisting of PvP, mannitol, polyethylene glycols, glycerides, and ethyl cellulose.

35. The microballs of claim 33 wherein the polymer material if 50% lactide and 50% glycolide.

* * * * *

UNITED STATES PATENT AND TRADEMARK OFFICE
CERTIFICATE OF CORRECTION

PATENT NO. : 5,213,812

DATED : May 25, 1993

INVENTOR(S) : Jean-Marc Ruiz

It is certified that error appears in the above-identified patent and that said Letters Patent is hereby corrected as shown below:

Column 6, line 35, change "an" to --a--.

Column 7, line 20 (claim 5), change "pamoater" to --pamoate--.

Column 7, line 66 (claim 11), change "if" to --is--.

Column 8, line 6 (claim 14), delete ",".

Column 10, line 14 (claim 35), change "if" to --is--.

Signed and Sealed this

Twenty-eighth Day of December, 1993

Attest:

BRUCE LEHMAN

*Attesting Officer*  *Commissioner of Patents and Trademarks*